United States Patent [19]

Drent

[11] Patent Number: 5,128,475
[45] Date of Patent: Jul. 7, 1992

[54] PREPARATION OF AMIDES

[75] Inventor: Eit Drent, Amsterdam, Netherlands

[73] Assignee: Shell Oil Company, Houston, Tex.

[21] Appl. No.: 535,691

[22] Filed: Jun. 11, 1990

[30] Foreign Application Priority Data

Feb. 5, 1990 [GB] United Kingdom ............... 9002522

[51] Int. Cl.$^5$ .................. C07D 213/75; C07D 229/40; C07D 231/10; C07D 233/36
[52] U.S. Cl. ..................................... 546/309; 560/37; 564/123; 564/132; 564/155; 564/207
[58] Field of Search ................. 560/37, 123, 132, 155, 560/207; 546/309

[56] References Cited

FOREIGN PATENT DOCUMENTS 2216036 3/1988 United Kingdom ............... 564/207

*Primary Examiner*—Alan L. Rotman

[57] ABSTRACT

A process for the preparation of an amide, which comprises reacting an acetylenically or olefinically unsaturated compound with carbon monoxide and a nitrogen compound selected from ammonia and a primary or secondary amine or amide, in the presence of a catalyst system which comprises:
a) a source of a Group VIII metal,
b) a phosphine having an aromatic substituent which contains an imino nitrogen atom, and
c) a protonic acid.

7 Claims, No Drawings

PREPARATION OF AMIDES

FIELD OF THE INVENTION

The present invention relates to a carbonylation process for the preparation of amides.

BACKGROUND OF THE INVENTION

J. Falbe, "New Syntheses with Carbon Monoxide", Springer Verlag, Berlin Heidelberg New York, 1980 reviews known carbonylation processes for the preparation of amides. In the known processes, generally an acetylene or olefin is reacted with carbon monoxide and an amine or amide in the presence of a carbonylation catalyst. The carbonylation catalyst typically comprises a source of a Group VIII metal. Several of the carbonylation catalysts also comprise a ligand, for example pyridine or a phosphine.

British Pat. No. GB 2,216,036 discloses a process for the carbo-amination or carbo-amidation of olefins, which process comprises contacting an olefinically unsaturated compound in the liquid phase with carbon monoxide or a carbon monoxide-containing fluid and a compound having the structure H—NR$^1$R$^2$, wherein R$^1$ and R$^2$ are each independently selected from hydrogen, a hydrocarbon group or a group —C(O)—R$^3$, in which R$^3$ independently may be hydrogen or a hydrocarbon group, or R$^1$ and R$^2$, together with the nitrogen atom to which they are attached, form a heterocyclic group, the hydrocarbon moieties R$^1$, R$^2$ and/or R$^3$ optionally containing as further reactive groups one or more primary or secondary amino and/or aminocarbonyl groups, in the presence of a catalyst system obtainable by combining:

component (a):—a ruthenium compound, and
component (b):—a compound having an anion of an acid with pKa value <3.5 (measured at 25° C. in aqueous solution).

The reaction rates reported in the Examples in GB Pat. No. 2,216,036 are in general low.

It has now been found that amides can be prepared at a good reaction rate using a carbonylation catalyst which comprises a particular nitrogen-containing phosphine ligand.

SUMMARY OF THE INVENTION

The present invention provides a process for the preparation of an amide, which comprises reacting an acetylenically or olefinically unsaturated compound with carbon monoxide and a nitrogen compound selected from ammonia and a primary or secondary amine or amide, in the presence of a catalyst system which comprises:

a) a source of a Group VIII metal,
b) a phosphine having an aromatic substituent which contains an imino nitrogen atom, and
c) a protonic acid.

It has been found that the process according to the invention affords amides at a substantially higher rate than the process of GB Pat. No. 2,216,036.

DESCRIPTION OF THE PREFERRED EMBODIMENTS

The catalyst system used in the process according to the invention comprises a source of a Group VIII metal. The source of a Group VIII metal may be the metallic element or, preferably, a Group VIII metal compound.

Examples of Group VIII metals are iron, cobalt, nickel, ruthenium, rhodium, palladium, iridium and platinum.

The catalyst system according to the invention preferably comprises a source of palladium.

Examples of compounds of Group VIII metals include salts, for example salts of nitric acid; sulfuric acid; sulfonic acids; phosphonic acids; perhalic acids; carboxylic acids such as alkane carboxylic acids having not more than 12 carbon atoms, e.g. acetic acid; and hydrohalic acids. Since halide ions can be corrosive, salts of hydrohalic acids are not preferred. Other examples of compounds of Group VIII metals include complexes, such as complexes with acetylacetonate, phosphines and/or carbon monoxide. For example the compound of a Group VIII metal may be palladium acetylacetonate, tetrakis-triphenylphosphinepalladium, bis-tri-o-tolylphosphinepalladium acetate, bis-diphenyl-2-pyridylphosphinepalladium acetate, tetrakis-diphenyl-2-pyridylphosphinepalladium, bis-di-o-tolylpyridyl-phosphinepalladium acetate, or bis-diphenylpyridyl-phosphinepalladium sulphate.

The catalyst system used in the process according to the invention further comprises a phosphine having an aromatic substituent which contains an imino nitrogen atom.

As used herein, the term "imino nitrogen atom" means a nitrogen atom which may be represented in the structural formula of the aromatic substituent containing it by the formula

For example, if the aromatic substituent is a pyridyl group, the structural formula of the aromatic substituent is

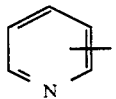

The phosphine preferably comprises one or two phosphorus atoms. Each phosphorus atom has three substituents. At least one of these substituents is an aromatic substituent which contains an imino nitrogen atom. The remaining substituents are preferably selected from optionally substituted aliphatic and aromatic hydrocarbyl groups. When the phosphine comprises more than one phosphorus atom, it is possible for one substituent to be shared by more than one phosphorus atom, as for example in

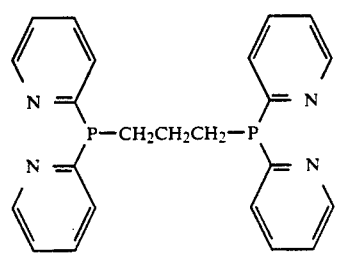

The aromatic substituent which contains an imino nitrogen is preferably a 6-membered ring containing one, two or three nitrogen atoms. The aromatic substituent may itself be optionally substituted.

When a substituent is said to be "optionally substituted" in this specification, unless stated otherwise, the substituent may be unsubstituted or substituted by one or more substituents. Examples of suitable substituents include halogen atoms; alkyl groups; alkoxy groups; haloalkyl groups; haloalkoxy groups; acyl groups; acyloxy groups; tertiary amino groups; hydroxy groups; nitrile groups; acylamino groups; and aromatic hydrocarbyl groups.

An aliphatic hydrocarbyl group is preferably an alkyl group or a cycloalkyl group.

An alkyl group, as such or in an alkoxy group, is preferably a $C_{1-10}$ alkyl group, more preferably a $C_{1-6}$ alkyl group. Examples of alkyl groups are methyl, ethyl, n-propyl, isopropyl, n-butyl, iso-butyl and tert-butyl.

A cycloalkyl group is preferably a $C_{3-6}$ cycloalkyl group, for example cyclopentyl or cyclohexyl.

An aromatic hydrocarbyl group is preferably a phenyl group.

A halogen atom, as such or in a haloalkyl group, is preferably a fluorine, chlorine or bromine atom.

An acyl group in an acyl, acyloxy or acylamino group is preferably a $C_{2-5}$ alkanoyl group such as acetyl.

A tertiary amino group is preferably a dialkylamino group.

Examples of aromatic substituents containing an imino nitrogen atom are pyridyl, pyrazinyl, quinolyl, isoquinolyl, pyrimidinyl, pyridazinyl, cinnolinyl, triazinyl, quinoxalinyl, and quinazolinyl. Preferred substituents are pyridyl and pyrimidyl.

An imino group in an aromatic substituent containing an imino nitrogen atom is preferably connected to a phosphorus atom through a single bridging carbon atom. For example, if the aromatic substituent is a pyridyl group, it is preferably connected through the carbon atom at the 2-position in the pyridyl group. Accordingly, examples of preferred aromatic substituents containing an imino nitrogen atom are 2-pyridyl; 2-pyrazinyl; 2-quinolyl; 1-isoquinolyl; 3-isoquinolyl; 2-pyrimidinyl; 3-pyridazinyl; 3-cinnolinyl; 2-triazinyl; 2-quinoxalinyl; and 2-quinazolinyl. 2-Pyridyl and 2-pyrimidyl are particularly preferred.

When the phosphine contains one phosphorus atom, it may conveniently be represented by the general formula

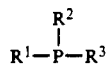  (I)

in which $R^1$ represents an aromatic substituent containing an imino nitrogen atom, and $R^2$ and $R^3$, which may be the same or different, represent a group $R^1$ or an optionally substituted aliphatic or aromatic hydrocarbyl group.

Examples of phosphines are:
bisphenyl-(2-pyridyl)phosphine,
bis(2-pyridyl)phenylphosphine,
tris(2-pyridyl)phosphine,
diphenyl-(6-methyl-2-pyridyl)phosphine,
diphenyl-(3-methyl-2-pyridyl)phosphine,
phenyl-bis(6-methyl-2-pyridyl)phosphine,
tris(6-methyl-2-pyridyl)phosphine,
diphenyl-(4,6-dimethyl-2-pyridyl)phosphine,
diphenyl-(6-methoxy-2-pyridyl)phosphine,
di(n-butyl)-2-pyridylphosphine,
dimethyl-2-pyridylphosphine,
methylphenyl-2-pyridylphosphine,
n-butyl-2-pyridylphosphine,
n-butyl(4-methoxyphenyl) (2-pyridyl)phosphine,
methyldi(2-pyridyl)phosphine,
bis(6-ethoxy-2-pyridyl)phenylphosphine,
bis(6-chloro-2-pyridyl)phenylphosphine, and
bis(6-bromo-2-pyridyl)phenylphosphine.

The catalyst system used in the process according to the invention further comprises a protonic acid. The function of the protonic acid is to provide a source of protons. Accordingly, the protonic acid may be generated in situ.

Preferably, the protonic acid is selected from acids having a non-coordinating anion. Examples of such acids include sulfuric acid; a sulfonic acid, e.g. an optionally substituted hydrocarbylsulphonic acid such as an optionally substituted arylsulfonic acid, e.g. benzenesulfonic acid, p-toluenesulfonic acid, naphthalenesulfonic acid, an optionally substituted alkylsulfonic acid such as an alkylsulfonic acid, e.g. methane-sulfonic acid or tertiary butylsulfonic acid, or a substituted alkanesulfonic acid such as 2-hydroxypropanesulfonic acid, trifluoromethane-sulfonic acid, chlorosulfonic acid or fluorosulfonic acid; a phosphonic acid, e.g. orthophosphonic acid, pyrophosphonic acid or benzenephosphonic acid; a carboxylic acid, e.g. chloroacetic acid, dichloroacetic acid, trichloroacetic acid, trifluoroacetic acid, oxalic acid or terephthalic acid; or a perhalic acid such as perchloric acid. The protonic acid may also be a sulfonated ion exchange resin.

The catalyst system used in the process according to the invention may be homogeneous or heterogeneous. Preferably it is homogeneous.

The ratio of the number of moles of phosphine per gram atom of Group VIII metal is not critical. Preferably it is in the range of from 1 to 1,000, more preferably from 2 to 500, especially from 10 to 100.

The ratio of the number of moles of phosphine per mole of protonic acid is not critical. Preferably it is in the range of from about 0.1 to about 50, more preferably from about 0.5 to about 25, especially from about 1 to about 10.

The process according to the invention is conveniently effected in the liquid phase. A separate solvent is not essential. Solvents suitable for use in the process according to the invention include for example, sulfoxides and sulfones, for example dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, xylenes; esters such as methylacetate and butyrolactone; ketones such as acetone or methyl isobutyl ketone and ethers such as anisole, 2,5,8-trioxanone (also referred to as diglyme), diphenyl ether and diisopropyl ether, and tertiary amides such as N-methylpyrolidone.

The process according to the present invention is conveniently effected at a temperature in the range of from about 10° C. to about 200° C., preferably from about 20° C. to about 130° C.

The process according to the invention is preferably effected at a pressure of from about 1 bar to about 70 bar. Pressures higher than about 100 bar may be used, but are generally economically unattractive on account of special apparatus requirements.

The molar ratio of the nitrogen compound reactants to the unsaturated hydrocarbon may vary between wide limits and generally lies within the range of about 0.01:1 to about 100:1.

The quantity of the Group VIII metal is not critical. Preferably, quantities are used within the range of $10^{-7}$ to $10^{-1}$ gram atom Group VIII metal per mol of unsaturated compound.

The carbon monoxide required for the process according to the present invention may be used in a practically pure form or diluted with an inert gas, for example nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than 5% v.

The acetylenically or olefinically unsaturated compound is preferably a substituted or unsubstituted alkyne, alkene or cycloalkene having from 2 to 30, preferably from 2 to 10 carbon atoms per molecule, and one, two or more acetylenic and/or olefinic carbon-carbon bonds.

Preferably the acetylenically or olefinically unsaturated compound is alpha-unsaturated.

Suitable substituents on the unsaturated compound include halogen atoms and cyano, acetoxy, alkoxy and aryl groups.

Examples of alkynes are: ethyne, propyne, phenylacetylene, 1-butyne, 2-butyne, 1-pentyne, 1-hexyne, 1-heptyne, 1-octyne, 2-octyne, 4-octyne, 5-methyl-3-heptyne, 4-propyl-2-pentyne, 1-nonyne, benzylethyne and cyclohexylethyne.

Examples of alkenes are ethene, propene, 1-butene, 2-butene, 1-pentene, 1-hexene, 1-heptene, 1-octene, 2-octene, cyclohexene and norbornadiene.

The nitrogen compound is preferably a compound of general formula

$$HNR^5R^6 \qquad (II)$$

in which each of $R^5$ and $R^6$ independently represents a hydrogen atom or an optionally substituted alkyl, cycloalkyl, aryl, aromatic heterocyclic, or acyl group, or $R^5$ and $R^6$ together with the nitrogen atom to which they are attached form a ring.

An alkyl group preferably has from 1 to 30 carbon atoms, more preferably from 1 to 20 carbon atoms, and most preferably from 1 to 10 carbon atoms. Examples of alkyl groups are methyl, ethyl, propyl, butyl, pentyl, hexyl, heptyl, octyl, nonyl and decyl.

A cycloalkyl group preferably has from 3 to 7 carbon atoms. Examples of cycloalkyl groups are cyclopropyl, cyclobutyl, cyclopentyl and cyclohexyl.

An aryl group is preferably a phenyl or naphthyl group.

An aromatic heterocyclic group is preferably a 5- or 6-membered ring containing at least one oxygen, nitrogen and/or sulphur atom. Examples of heterocylic groups are benzimidazole, triazole, quinoxaline, pyridazine, thiophene, purine, triazine, cinnoline, quinazoline, imidazole, thiazole, oxazole, pyrazole, oxazole, isothiazole, pyridine, pyrrole, quinoline, indole, pyrimidine, furan, pyrazine and benzofuran.

An acyl group is preferably an alkanoyl group having from 1 to 30, more preferably from 1 to 10 carbon atoms, such as acetyl or propanoyl; or an aroyl group such as benzoyl.

A ring formed by $R^5$, $R^6$ and the nitrogen atom to which they are attached may be, for example, pyrrolidine, pyrrolidone, morpholine, piperidine, indoline or piperazine.

Each of the groups $R^5$ and $R^6$ may be substituted or unsubstituted by one or more substituents. The substituents are preferably selected from a halogen atom, e.g. fluorine, chlorine or bromine; an alkyl group, e.g. methyl, ethyl, propyl or butyl; an alkoxy group, e.g. methoxy, ethoxy, propoxy or butoxy; a haloalkyl group, e.g. trifluoromethyl; a haloalkoxy group, e.g. trifluoromethoxy; a nitro group; a cyano group; an acyl group, e.g. acetyl; an acyloxy group, e.g. acetoxy; an amino group; an alkylamino group, e.g. methylamino; a dialkylamino group, e.g. dimethylamino; an amido group, e.g. acetamido; a sulfonic acid group; a hydroxyl group; a carboxyl group; and an aryl group such as phenyl.

Examples of compounds of general formula II include ammonia, alkylamines such as methylamine, ethylamine; propylamines and butylamines; dialkylamines such as dimethylamine and diethylamine; anilines such as aniline, 1,4-diaminobenzene, aminopyridine and 1,3-diaminobenzene; and alkanoylamines such as acetamide and 2-pyrrolidone.

When the unsaturated compound is an acetylenically unsaturated compound, the nitrogen compound is preferably an aniline.

When ammonia or an alkylamine is used, the process is preferably effected in the presence of a carboxylic acid, for example acetic or propionic acid. Most preferably an excess of carboxylic acid over ammonia or alkylamine is used.

The nitrogen compound may be generated in situ from the corresponding acid addition salt.

The process according to the invention may be carried out continuously or batchwise.

The catalyst systems used in the process according to the invention may be prepared by any convenient method. Thus, they may be prepared by combining a separate Group VIII metal compound, the phosphine (I) and the protonic acid. Alternatively, they may be prepared by combining a Group VIII metal compound and an acid addition salt of the phosphine. Alternatively, they may be prepared from a Group VIII metal compound which is a complex of a Group VIII metal with the phosphine, and/or the protonic acid.

Phosphines having an aromatic substituent which contains an imino nitrogen atom are known in the art. They are conveniently prepared by reacting a phosphorus halide or alkali metal phosphine with a appropriate alkali metal or halide derivative of a heterocyclic compound containing an imino nitrogen atom.

The invention will now be described by the following Examples which are intended to be illustrative and which are not to be construed as limiting the invention.

In the Examples, the selectivity to a certain compound, expressed as a percentage, is defined as 100 a/b, in which "a" is the amount of acetylenically or olefinically unsaturated compound that has been converted into a certain compound and "b" is the total amount of that unsaturated compound that has been converted.

Preparation 1

Preparation of diphenyl-(6-methyl-2-pyridyl)-phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 10 g 2-bromo-6-methtylpyridine in 15 ml diethyl ether; during this addition, the temperature was kept at −40° C. After the addition, the temperature was raised to −5° C., kept there for 5 minutes, and then lowered again to −40° C. A solution of 12.8 g chlorodiphenylphosphine in 15 ml diethyl ether was added in the course of 15 minutes to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50 ml portions of dichloromethane, the organic reactions were combined, and the solvent removed in vacuo. The residue was crystallized from toluene/hexane to afford 12 g (75%) of diphenyl-(6-methyl-2-pyridyl)-phospine as off-white crystals. The product was characterized by $^{31}$P NMR: $\delta_p = -5.6$ ppm.

Preparation 2

Preparation of diphenyl-(3-methyl-2-pyridyl)-phosphine

This compound was prepared as described in Preparation 1, but using 10.0 g 2-bromo-3-methylpyridine instead of the 2-bromo-6-methylpyridine. It was characterized by $^{31}$P NMR: $\delta_p = -8.1$ ppm.

Preparation 3

Preparation of phenyl-bis(6-methyl-2-pyridyl)-phosphine

This compound was prepared as described in Preparation 1, but using 5.2 g phenyldichlorophosphine instead of the chlorodiphenylphosphine. It was characterized by $^{31}$P NMR: $\delta_p = -5.1$ ppm.

Preparation 4

Preparation of tris(6-methyl-2-pyridyl)-phosphine

This compound was prepared as described in Preparation 1, but using 2.7 g phosphorus trichloride instead of the chlorodiphenylphosphine. It was characterized by $^{31}$P NMR: $\delta_p = -3.8$ ppm.

Preparation 5

Preparation of diphenyl-(4,6-dimethyl-2-pyridyl)-phosphine

This compound was prepared as described in Preparation 1, but using 10.8 g 2-bromo-4,6-dimethylpyridine instead of the 2-bromo-6-methylpyridine. It was characterized by $^{31}$P NMR: $\delta_p = -5.6$ ppm.

Preparation 6

Preparation diphenyl-(6-methoxy-2-pyridyl)-phosphine 2.7 g Sodium was added to 100 ml liquid ammonia at −80° C., and then 15.2 g triphenylphosphine was added in 6 portions with stirring. The solution was slowly warmed to −40° C., kept at that temperature for 30 min, and then cooled again to −80° C. Then, 3.1 g ammonium chloride was added to the stirred solution, followed by 10.9 g 2-bromo-6-methoxypyridine in three portions. The cooling bath was removed and the ammonia was allowed to evaporate. The residue was worked up with water/dichloromethane as described in Preparation 1. Crystallization from hexane afforded 7 g of a somewhat impure product (characterized by $^{31}$P NMR: $\delta_p = -4.4$ ppm).

Preparation 7

Preparation of di(n-butyl)-2-pyridyl phosphine

To a magnetically stirred solution of 2.5 g phenyl(2-pyridyl)$_2$P in 20 mol tetrahydrofuran, cooled to −80° C., was added in the course of 10 min 5.9 ml of a 1.6M solution of n-butylLi in hexane. The resulting deep-red solution was allowed to warm to room temperature, and analysis of the solution by $^{31}$P NMR showed it to contain the phosphide (n-butyl)(2-pyridyl)PLi as the only phosphorus-containing compound ($\delta_p = -16.3$ ppm).

The solution was cooled to −40° C. and a solution of 1.3 g 1-bromobutane in 10 ml tetrahydrofuran was added. The mixture was again warmed to room temperature, the solvents were removed in vacuo, and 25 ml of diethylether and 10 ml of water were added. After 10 min of stirring, the organic layer was separated and the water layer was extracted with 10 ml of ether. The organic layers were combined and the solvent was removed in vacuo (66 Pa). The resulting light-yellow liquid was analyzed by $^1$H, $^{13}$C and $^{31}$P NMR and shown to consist of a 1:1 (molar ratio) mixture of 2-phenylpyridine and (n-butyl)$_2$(2-pyridyl)P ($\delta_p = -19.5$ ppm).

Preparation 8

Preparation of dimethyl 2-pyridyl phosphine andmethylphenyl-2-pyridyl phosphine The method of Preparation 7 was repeated, except that a 1.6M solution of methylLi in diethylether was used instead of the n-butylLi solution, and 1.3 g iodomethane instead of the bromobutane. The reaction product was a mixture of (methyl)$_2$- (2-pyridyl)P, methyl phenyl 2-pyridylP and 2-phenyl pyridine in the approximate ratio 70:30:60, from which the (methyl)$_2$(2-pyridyl)P was isolated by distillation.

The physical characteristics of the products were $\delta_p = -41.2$ ppm (dimethyl-2-pyridylphosphine) and $\delta_p = -24.1$ ppm (methylphenyl2-pyridylphosphine).

Preparation 9

Preparation of n-butyl tert-butyl 2-pyridyl phosphine

The method of Preparation 7 was repeated, except that 5.6 ml of a 1.7M solution of t-butylLi in pentane was used instead of the n-butylLi solution. The final product was identified as n-butyl t-butyl 2-pyridylP by NMR analysis ($\delta_p = 7.4$ ppm).

Preparation 10

Preparation of dimethyl 2-pyridylphosphine

The method of Preparation 8 was repeated, except that 1.91 g methyl(2-pyridyl)$_2$P and only 0.7 g iodomethane were used. Workup as described in Example 1 afforded dimethyl 2-pyridyl phosphine, which was further purified by distillation (65% yield). ($\delta_p = -41.2$ ppm).

Preparation 11

Preparation of n-butyl(4-methoxyphenyl)(2-pyridyl)phosphine

All manipulations were carried out in an inert atmosphere (nitrogen or argon). Solvents were dried and distilled prior to use. 18 ml of a 1.6M n-butyllithium solution in hexane was added to 30 ml diethyl ether, and the mixture was cooled to −40° C. To the stirred mixture was added in the course of 20 minutes a solution of 4.6 g 2-bromopyridine in 15 ml diethyl ether; during this addition, the temperature was kept at −40° C. After the addition, the temperature was raised to −5° C., kept there for 5 minutes, and then lowered again to −40° C. The resulting solution was added to a cooled (−40° C.) solution of 7.6 g 4-methoxyphenyl-bis(2-pyridyl)phosphine in 30 ml THF. The mixture was warmed to room temperature. After stirring for 10 minutes, the solvents were removed in vacuo. Water (25 ml) and dichloromethane (25 ml) were added. After 5 minutes of vigorous stirring, the dichloromethane layer was separated. The water layer was extracted with two 25-ml portions of dichloromethane, the organic fractions were combined, and the solvent removed in vacuo. The residue was distilled, giving 4.7 g (60%) of (n-butyl) (4-methoxyphenyl) (2-pyridyl)phosphine as a yellowish liquid. The product was characterized by $^{31}P$ NMR: $\delta_p = -14.9$ ppm.

In this experiment, n-butyllithium is believed to react with 2-bromopyridine to afford a mixture of n-butylbromide and 2-pyridyllithium. Then the 2-pyridyllithium reacts with 4-methoxy-bis(2-pyridyl)phosphine to afford 4-methoxyphenyl(2-pyridyl)lithium phosphide (and 2,2'-bipyridine). The lithium phosphide then reacts with n-butylbromide to afford (n-butyl) (4-methoxyphenyl) (2-pyridyl)phosphine.

Preparation 12

Preparation of methyl di(2-pyridyl)phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 9.2 g 2-bromopyridine in 15 ml diethyl ether; during this addition, the temperature was kept at −40° C. After the addition, the temperature was raised to −5° C., kept there for 5 minutes, and then lowered again to −40° C. A solution of 3.4 g methyldichlorophosphine in 15 ml diethyl ether was added to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50-ml portions of dichloromethane, the organic fractions were combined, and the solvent removed in vacuo. The residue was distilled, giving 4.0 g (68%) of methyl-bis(2-pyridyl)phosphine as a yellowish liquid. The product was characterized by $^{31}P$ NMR: $\delta_p = -20.5$ ppm.

EXAMPLE 1

A 250 ml stainless steel, magnetically stirred autoclave was filled with 0.1 mmol palladium(II) acetate, 2 mmol bisphenyl(2-pyridyl)phosphine, 3 mmol p-toluenesulfonic acid, 30 ml N-methylpyrrolidone and 20 ml aniline. Air was then evacuated from the autoclave, and 30 ml propyne were added. The autoclave was then pressurized with 60 bar carbon monoxide, sealed and heated to 70° C. After 1½ hours reaction time, a sample of the contents of the autoclave was withdrawn and analyzed by gas-liquid chromatography. The analysis revealed that a-methyl acrylanilide had been formed with a selectivity of 99%. The mean conversion rate was calculated to be 1500 moles propyne/gram atom Pd/hour.

EXAMPLE 2

A 250 ml stainless steel, magnetically stirred autoclave was filled with 0.1 mmol palladium(II) acetate, 5 mmol bisphenyl(2-pyridyl)phosphine, 4 mmol p-toluenesulfonic acid, 50 ml N-methylpyrrolidone and 10 ml aniline. Air was then evacuated from the autoclave. The autoclave was then pressurized with 30 bar carbon monoxide and 20 bar ethene, sealed and heated to 90° C. After 5 hours reaction time, a sample of the contents of the autoclave was withdrawn and analyzed by gas-liquid chromatography. The analysis revealed that propanoyl anilide had been formed with a selectivity of 99.9%. The mean conversion rate was calculated to be 350 moles ethene/gram atom Pd/hour.

EXAMPLE 3

The method of Example 2 was repeated, but using 50 mmol norbornadiene instead of ethene and 100 mmol aniline instead of 10 ml, pressurizing with 40 bar carbon monoxide and heating to 70° C. instead of 90° C. A sample withdrawn after a reaction time of 1 hour revealed that the following compounds had been formed with selectivities of 70% and 30% respectively:

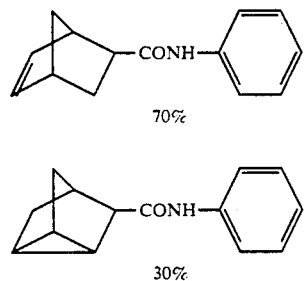

The mean conversion rate was calculated to be 1,000 moles norbornadiene/gram atom Pd/hour.

EXAMPLE 4

The method of Example 3 was repeated, but with heating to only 50° C. Analysis of a sample of the contents of the autoclave after 5 hours reaction time revealed that the following compounds had been formed with selectivities of 90% and 10% respectively:

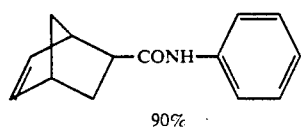

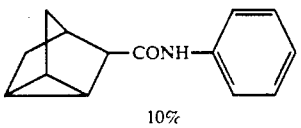
10%

The mean conversion rate was calculated to be 300 moles norbornadiene/gram atom Pd/hour.

EXAMPLE 5

The method of Example 3 was repeated, but heating at 50° C. for ½ hour and then 100° C. for 4½ hours. Analysis of the reaction product revealed that the following compound had been formed with 90% selectivity:

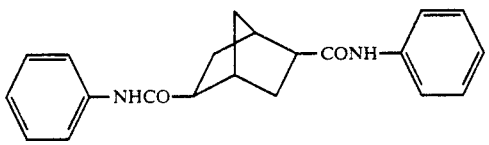

The mean conversion rate was calculated to be 1,000 moles norbornadiene/gram atom Pd/hour.

Comparative Example A

The method of Example 2 was repeated, but using triphenylphosphine instead of bisphenyl(2-pyridyl)-phosphine, and 20 ml aniline instead of 10 ml aniline. Propanoyl anilide was formed, but the mean conversion rate was calculated to be less than 10 moles ethene/gram atom Pd/hour.

EXAMPLE 6

The method of Example 2 was repeated, but using 10 ml N-methyl acetamide instead of aniline. N-methyl, N-acetyl propionamide was found to have been formed with a selectivity of 98%. The mean conversion rate was calculated to be 200 moles ethene/gram atom Pd/hour.

EXAMPLE 7

The method of Example 2 was repeated, but using 10 ml 2-pyrrolidone instead of aniline. N-propanoyl pyrrolidone was found to have been formed with a selectivity of 95%. The mean conversion rate was calculated to be 100 moles ethene/gram atom Pd/hour.

EXAMPLE 8

A 250 ml stainless steel, magnetically stirred autoclave was filled with 0.1 mmol palladium(II) acetate, 5 mmol bisphenyl(2-pyridyl)phosphine, 4 mmol p-toluenesulfonic acid, 50 ml propionic acid and 10 ml n-butylamine. Air was then evacuated from the autoclave. The autoclave was then pressurized with 30 bar carbon monoxide and 20 bar ethene, sealed and heated to 110° C. After 1½ hours reaction time, a sample of the contents of the autoclave was withdrawn and analyzed by gas-liquid chromatography. The analysis revealed that N-butyl propionamide had been formed with a selectivity (based on amine) of >95%, together with propionic anhydride. The mean conversion rate was calculated to be 1,500 moles ethene/gram atom Pd/hour.

Comparative Example B

The method of Example 8 was repeated, but using triphenylphosphine instead of bisphenyl(2-pyridyl)-phosphine. After ½ hour no reaction was observed.

EXAMPLE 9

The method of Example 8 was repeated, but using 50 mmol 1,2-diaminoethane instead of 1-butylamine, and heating for 2 hours. The following products were formed in the ratio indicated:

  (3)

  (1)

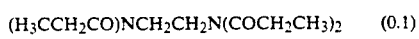  (0.1)

together with propionic anhydride.

EXAMPLE 10

The method of Example 8 was repeated, but using 10 g ammonium acetate instead of 1-butylamine, and heating to 90° C. instead of 110° C. Propionamide was obtained with a selectivity of >90%, based on ammonium acetate, together with acetic acid and propionic anhydride. The mean conversion rate was calculated to be 2,500 moles/gram atom Pd/hour.

EXAMPLE 11

The method of Example 8 was repeated but using 15 g 4-methoxycarbonylaniline instead of 1-butylamine, and heating at 90° C. for 1½ hours. N-propionyl(4-methoxycarbonyl)anilide was formed with a selectivity of 100%, based on aniline, together with propionic anhydride. The mean conversion rate was calculated to be 2,000 moles ethene/gram atom Pd/hour.

EXAMPLE 12

The method of Example 2 was repeated, but using 10 g 2-aminoethanesulfonic acid instead of aniline, and heating at 100° C. for 5 hours. N-propionylamidoe-thanesulphonic acid was formed with a selectivity of about 80%. The mean conversion rate was calculated to be 300 moles ethene/gram atom Pd/hour.

EXAMPLE 13

The method of Example 8 was repeated, but using 10 g 4-aminopyridine instead of 1-butylamine. 4-(N-propionylamido)pyridine was formed with a selectivity, based on amine, of 100%, together with propionyl anhydride. The mean conversion rate was calculated to be 500 moles ethene/gram atom Pd/hour.

EXAMPLE 14

The method of Example 3 was repeated, but using 25 mmol 1,4-diaminobenzene and 25 mmol 1,3-diaminobenzene instead of aniline and heating for 1 hour at 50° C., then 4 hours at 110° C. A polyamide was obtained.

What is claimed is:

1. A process for the preparation of a member selected from the group consisting of an alkyl-carboxamide, a cycloalkyl carboxamide, an aryl carboxamide and an aromatic heterocyclic carboxamide, which comprises reacting an acetylenically or olefinically unsaturated compound with carbon monoxide and a nitrogen compound selected from the group consisting of ammonia, a primary amine, a secondary amine, in the presence of a catalyst system which comprises:
a) a palladium compound,
b) a phosphine selected from a 2-pyridylphosphine and a 2-pyrimidinylphosphine, and
c) a protonic acid.

2. The process of claim 1 wherein the protonic acid is selected from the group consisting of sulfuric acid, a sulfonic acid, a phosphonic acid, a carboxylic acid, or a perhalic acid.

3. The process of claim 1 wherein the ratio of the number of moles of phosphine per gram atom of Group VIII metal is in the range of from about 2 to about 500, and the ratio of the number of moles of phosphine per mole of protonic acid is in the range of from about 0.5 to about 25.

4. The process of claim 1 wherein the temperature is in the range of from about 20° C. to about 130° C., and the pressure is in the range of from about 1 bar to about 70 bar.

5. The process of claim 1 wherein the acetylenically or olefinically unsaturated compound is an alkene, cycloalkene or alkyne having from 2 to 10 carbon atoms.

6. The process of claim 1 wherein the nitrogen compound is a compound of general formula $$HNR^5R^6 \qquad (II)$$

in which each of $R^5$ and $R^6$ independently represents a hydrogen atom, or an alkyl, cycloalkyl, aryl, aromatic heterocyclic, or $C_{2-5}$ alkanoyl group.

7. The process of claim 1 wherien the unsaturated compouns is an acetylenically unsaturated compound, and the nitrogen compound is an aniline.

* * * * *